United States Patent [19]

McMahon et al.

[11] 4,250,340

[45] Feb. 10, 1981

[54] PROCESS FOR PREPARING ARALKYL HALIDES

[75] Inventors: Philip J. McMahon, Wolverhampton; Frank S. Yates, Brocton, both of England

[73] Assignee: Croda Synthetic Chemicals Limited, Four Ashes West Midlands, England

[21] Appl. No.: 971,470

[22] Filed: Dec. 20, 1978

[30] Foreign Application Priority Data

Dec. 22, 1977 [GB] United Kingdom .............. 53518/77

[51] Int. Cl.³ ............................................ C07C 41/22
[52] U.S. Cl. ................................................. 568/639
[58] Field of Search ....................... 260/600; 568/639

[56] References Cited

U.S. PATENT DOCUMENTS

| | | | |
|---|---|---|---|
| 4,085,147 | 4/1978 | Rosinger et al. ................ | 260/600 R |
| 4,108,904 | 8/1978 | Brown et al. .................... | 260/600 R |
| 4,146,737 | 3/1979 | Sheldon et al. ..................... | 568/639 |

OTHER PUBLICATIONS

Levenspiel, Chemical Reaction Engineering, (1962), 327–328.

*Primary Examiner*—Bernard Helfin
*Attorney, Agent, or Firm*—Lawrence Rosen

[57] ABSTRACT

A process for chlorinating m-phenoxytoluene by reaction with sulphuryl chloride in the presence of an initiator, in which the initiator is added not only at the beginning of, but also during, the reaction, and/or in which the initiator is a tert-butyl peralkanoate, and/or in which the reaction solvent is perchloroethylene and/or in which the m-phenoxytoluene and sulphuryl chloride are used in substantially equimolar amounts.

6 Claims, No Drawings

PROCESS FOR PREPARING ARALKYL HALIDES

This invention relates to processes for preparing m-phenoxybenzyl chloride, usually in admixture with m-phenoxybenzal chloride, from m-phenoxytoluene. This invention also relates to processes for converting the chloride or mixture of chlorides to m-phenoxybenzyl alcohol or m-phenoxybenzaldehyde. These last two compounds are of utility as intermediates in the preparation of synthetic pyrethroid insecticides.

The conversion of o- or p-phenoxytoluene to o- or p-phenoxybenzaldehyde, via the corresponding phenoxybenzyl bromide, is disclosed by G. Ito, Pharm. Bull. (Tokyo), 5, 390–405(1957).

British Patent Specification No. 1,442,533 discloses a process for preparing a mixture of m-phenoxybenzyl and m-phenoxybenzal chlorides by chlorinating m-phenoxytoluene at a temperature above 220° C. in the presence of a phosphorus halide. However, this process suffers from the disadvantage that undesirable amounts of ring-chlorinated products are obtained. Moreover, it is often desired to prepare m-phenoxybenzyl chloride with as little as possible of m-phenoxybenzal chloride.

After our priority application was filed, two Belgian Patent Specifications (Nos. 858,911 and 859,358) were published relating to processes for halogenating m-phenoxytoluene and converting m-phenoxybenzyl and m-phenoxybenzal halides to m-phenoxybenzaldehyde. Belgian Patent Specification No. 858,911 (published Mar. 21st 1978) discloses a process for preparing a mixture of a m-phenoxybenzyl halide and a m-phenoxybenzal halide by reacting m-phenoxytoluene in an inert solvent at about the boiling point of the solvent in the presence of a free radical initiator. It is stated that it is essential for from 1.2 to 2 moles of the halogenating agent to be used per mole of m-phenoxytoluene and for 0.5 to 10% by weight of the initiator to be used. One of the given halogenating agents is sulphuryl chloride ($SO_2Cl_2$) which, in all the relevant examples, is added continuously over the course of the reaction. In all examples where an initiator is used, it is added in its entirety to the m-phenoxytoluene before the halogenating agent is added. The only illustrated reaction solvent for this process is carbon tetrachloride.

Belgian Patent Specification No. 859,358 (published Apr. 4th 1978) also discloses a process for preparing m-phenoxybenzyl chloride and m-phenoxybenzal chloride by the reaction of m-phenoxytoluene with sulphuryl chloride in the presence of a free radical initiator. It is stated that a molar excess of from 50 to 200% of sulphuryl chloride should be used in order to reduce ring chlorination to a minimum. While it is stated that chlorinated hydrocarbon solvents may be used, the only given example is carbon tetrachloride. Further, in the given examples, all the initiator is added at the start of the reaction. Examples of initiators include tert-butyl perbenzoate.

Belgian Patent Specification No. 851,048 discloses that a mixture of m-phenoxybenzyl and m-phenoxybenzal chlorides may be converted to m-phenoxybenzaldehyde under the conditions of a Sommelet reaction. The Sommelet reaction is well known, and a review by S. J. Angyal appears in Organic Reactions 8, 197–217(1954). The conversion of the mixture of mono- and di-chlorides derived from m-phenoxytoluene is also disclosed in Belgian Patent Specification No. 858,911 and supports the observation made by Libman et al, Zhurnal Prikladnoi Khimii, 39 (7), 1669–70 (1966), that a mixture of benzyl and benzal chlorides may be converted in one step to benzaldehyde. While it is known that the Sommelet reaction can be used to convert, say, benzyl chloride to benzaldehyde, it is also known that the dichloride is hydrolysed in the work-up which necessarily follows a Sommelet reaction. The conversion of m-phenoxybenzyl chloride to m-phenoxybenzaldehyde is disclosed in German Offenlegungsschrift No. 2,651,371.

The first of the processes to which this invention particularly relates is that in which a mixture of m-phenoxybenzyl chloride and m-phenoxybenzal chloride is prepared by reacting m-phenoxytoluene with, per mole thereof, from 1 to 2 moles of sulphuryl chloride in an excess of solvent and in the presence of a peroxide initiator, the sulphuryl chloride being added portionwise or continuously to the m-phenoxytoluene during the course of the reaction. Such a reaction is conveniently carried out at the boiling point of the solvent (usually a chlorinated solvent) and it provides a mixture of unreacted m-phenoxytoluene, m-phenoxybenzyl chloride and m-phenoxybenzal chloride together with small amounts of nuclear chlorinated compounds. We have now found various ways in which such a reaction can be improved.

According to a first improvement, the initiator is added to the reaction mixture in amounts of from 1 to 4% at the start of the reaction and from 2 to 10% during the course of the reaction, the percentages being by weight based on the weight of m-phenoxytoluene. We have found that, in this manner, improved yields can be obtained over the case in which all the initiator is added at the start of the reaction.

It will be appreciated that the total amount of initiator which is used is from 3 to 14% by weight, based on the weight of m-phenoxytoluene. Greater amounts of initiator are unnecessary and wasteful, while smaller amounts may reduce the degree of conversion. Since it is necessary in any case to add the sulphuryl chloride portionwise or continuously, e.g. dropwise, during the course of the reaction, it is usually convenient to add the sulphuryl chloride and the initiator together. The initiator is most conveniently provided as a solution in the reaction solvent.

The amount of the initiator added during the course of the reaction will usually be about twice the amount added at the start of the reaction. It is preferred that more initiator should be added during the course of the reaction than at the start.

According to a second improvement, the initiator is a tert-butyl peralkanoate of the formula R—CO—O—O—C(CH$_3$)$_3$, wherein R is $C_{1-12}$ alkyl or $C_{1-12}$ alkoxy and has a half-life of 1 to 60 minutes at 115° to 123° C. The use of such initiators is preferred over those which have previously been proposed for use with sulphuryl chloride in the chlorination of m-phenoxytoluene. For example, they are particularly preferred over azo initiators and benzoyl peroxide in view of the fact that they give innocuous by-products which are volatile and easy to remove, they are relatively stable at the operational temperature, and they are soluble in the solvent and thus easier to handle. As has been explained above, this is of particular interest when the initiator is to be added during the course of the reaction as well as at the start.

R is preferably $C_{3-10}$ and is most preferably isopropoxy or octyl. Accordingly, the most preferred peroxide initiators for use in this invention are t-butylperoxy isopropyl carbonate (available as Trigonox BPIC) and t-butyl peroctoate. The initiator half-life is preferably about 30 minutes at 115° to 123° C.

According to a third improvement, the solvent is perchloroethylene (PCE), otherwise known as tetrachloroethylene. PCE is less volatile than carbon tetrachloride and is thus safer to handle. For example, the vapour pressure of PCE at 26° and 40° C. is 20 and 40 mm. Hg, respectively, while the respective values for carbon tetrachloride at the given temperatures are 114 and 216 mm. Hg. PCE is less hazardous in use than carbon tetrachloride, since their respective TLV are 100 and 10 ppm. Moreover, PCE has a lower solubility in water (0.02% w/w at 20° C.) than carbon tetrachloride (0.08% w/w at 20° C.) and has a higher boiling point. Losses during reaction are therefore smaller. Further, PCE gives a more favourable azeotropic mixture with water (82.8%PCE:17.2%$H_2O$ w/w; b.p. 88.5° C.) than carbon tetrachloride (95.9%$CCl_4$:4.1%$H_2O$ w/w; b.p. 66° C.). This last point is of particular importance since, when PCE is used, it is possible to achieve efficient and faster drying of recycled solvent. This is very important since the presence of water in the reaction mixture promotes ionic decomposition of the peroxide initiator.

Peroxide initiators, and particularly the preferred initiators for use in this invention, can conveniently be provided as a 1% w/v solution in PCE. Higher concentrations of initiator are undesirable since the peroxide decomposes more rapidly.

According to a fourth improvement, the proportions of m-phenoxytoluene and sulphuryl chloride are substantially equimolar, by which we mean that from 1 to 1.1 moles of sulphuryl chloride are used per mole of m-phenoxytoluene. As has been indicated above, the use of sulphuryl chloride in the chlorination of m-phenoxytoluene does not give 100% conversion and it is therefore usually desirable to recycle any unconverted starting material, usually after the chloride or mixture of chlorides has been converted to m-phenoxybenzaldehyde and the latter has been purified. On a continuous basis, therefore, higher conversion of the starting materials can be achieved by using substantially equimolar amounts of sulphuryl chloride and m-phenoxytoluene.

The chlorination reaction using sulphuryl chloride is preferably carried out at a temperature of at least 110° C. At such temperatures, the reaction time can be reduced to 4 hours or less.

As has already been indicated, the reaction should be carried out in an excess of solvent. Usually the ratio of solvent to substrate should be at least 10:1 w/w at the start of the reaction. Although lower amounts of solvent can be used, the reaction is inefficient if the excess of solvent is too little.

This invention provides an alternative, high temperature, process for the chlorination of m-phenoxytoluene. This reaction is carried out in the presence of a catalytic amount of a sulphur-containing catalyst and at a temperature which is, or is equivalent to, 200° to 280° C. at atmospheric pressure.

The catalyst is preferably an organic sulphur compound and more preferably a sulphide, e.g. a diaryl sulphide such as diphenyl sulphide.

The temperature of reaction for the greatest selectivity in the preparation of m-phenoxybenzyl chloride rather than m-phenoxybenzal chloride is critical and should normally be from 230° to 280° C. Most preferably, the temperature is about 250° C. The reaction may be carried out in glass but there are advantages in using stainless steel in that, although the conversion is somewhat reduced, the selectivity with regard to monochlorination is increased.

This reaction provides a source from which pure m-phenoxybenzyl chloride may be isolated by fractional distillation under reduced pressure. The unreacted m-phenoxytoluene is conveniently recycled to the chlorination, and this recycling may be carried out at this stage.

A particular advantage of this high temperature chlorination lies in that it may be carried out in the absence of a solvent, and it allows a high production rate for a given size of reactor when compared with the use of a solvent. The process may be conducted continuously or as a batch reaction.

As has been indicated above, m-phenoxybenzyl chloride, alone or in admixture with m-phenoxybenzal chloride, may be converted to m-phenoxybenzaldehyde by a Sommelet reaction, using hexamine (or ammonia and formaldehyde) and an aqueous organic acid. If the Sommelet reaction is carried out in the presence of other compounds such as unreacted m-phenoxytoluene, the crude m-phenoxybenzaldehyde is isolated by extraction with a suitable solvent such as diisopropyl ether and it may then be purified by preparing the corresponding bisulphite compound, washing it with solvent and subsequently regenerating the pure aldehyde by treatment with an acid or base. Alternatively, the bisulphite compound may be isolated and dried to obtain a pure material which can be converted directly to m-phenoxybenzaldehyde cyanohydrin by reaction with a cyanide such as sodium cyanide, thereby avoiding the additional stage of isolating the purified m-phenoxybenzaldehyde.

Purification processes involving the preparation of a bisulphite compound are well known. They are specifically applied to m-phenoxybenzaldehyde in Belgian Patent Specifications Nos. 851,048; 857,954; 858,127 and 858,911 and in German Offenlegungsschrift No. 2,651,371. Cyanohydrin preparation procedures are also well known. A specific application to the compounds disclosed herein is described in Belgian Patent Specification No. 858,127. m-Phenoxybenzaldehyde may be converted to pure m-phenoxybenzyl alcohol by an application of the Cannizzaro reaction in which m-phenoxybenzaldehyde is reduced and another aldehyde (formaldehyde) is simultaneously oxidised to the corresponding acid (formic acid). By using adsorbents to remove water and any coloured impurities, the m-phenoxybenzyl alcohol may be isolated in a high state of purity without the need for distillation. This avoids possible decomposition of a material of limited thermal stability. Such crossed Cannizzaro reactions are well known and are described in, for example, Organic Reactions 2, 109 and 113 (1944). A disclosure of the reaction as applied to the compounds disclosed herein is in British Patent Specification No. 1,442,533.

This invention provides an alternative procedure for preparing m-phenoxybenzyl alcohol, which comprises (1) reacting m-phenoxybenzyl chloride with an excess of a metal alkanoate in a phase-transfer reaction using a phase-transfer catalyst to form a m-phenoxybenzyl alkanoate and (2) reacting the m-phenoxybenzyl alkanoate with an excess of a metal hydroxide in a phase transfer reaction using a phase-transfer catalyst. A suitable feedstock for this phase-transfer reaction is substantially pure m-phenoxybenzyl chloride obtained by fractional distillation of the product of the chlorination of m-phenoxytoluene. A particularly suitable feedstock for the distillation is the product of the high temperature chlorination process described above, where the ratio of m-phenoxybenzyl chloride to m-phenoxybenzal chloride is high. The m-phenoxybenzyl chloride, with or preferably without a solvent, is reacted with, for example, aqueous sodium acetate at a moderate temperature, usually about 100° C., in the presence of a phase-transfer catalyst such as a quaternary ammonium halide. The m-phenoxybenzyl chloride is thereby converted to m-phenoxybenzyl acetate almost quantitatively without loss of the high purity of the starting material. By changing the aqueous phase, the acetate or other alkanoate which is prepared in the first step may then be hydrolysed using, for example, aqueous sodium hydroxide in a similar mild phase-transfer procedure. The hydrolysis takes place in almost quantitative yield and adsorptive processes are used to remove any impurities. For example, ion exchange may be used to remove the phase-transfer catalyst, charcoal may be used to remove any colour, and a molecular sieve may be used to remove water. The final product is of high purity.

Depending on the phase-transfer catalyst which is used, it may be unnecessary to add more for the hydrolysis as it can be retained in the m-phenoxybenzyl acetate layer. Preferred phase-transfer catalysts are tetrabutylammonium bromide and tricaprylmethylammonium chloride (which is very soluble in the organic layer).

If desired it is possible to convert the pure m-phenoxybenzyl alcohol to m-phenoxybenzaldehyde by a third phase-transfer process, parallel to that disclosed by Law and Freedman, Tetrahedron Letters 20, 1641–1644 (1976). For this procedure the m-phenoxybenzyl alcohol is conveniently dissolved in a solvent, preferably ethyl acetate, and oxidised in the presence of a phase-transfer catalyst. By suitable choice of catalyst it may be retained in the organic layer from the previous two stages. For this stage sodium hypochlorite is the oxidising agent of choice, being both cheap and effective. The m-phenoxybenzyldehyde produced in this way is purified by removal of both the phase-transfer catalyst and the solvent and, optionally, it may be distilled under reduced pressure without fractionation in order to remove any traces of coloured impurities.

The following Examples illustrate the invention, except for Example A which is provided by way of comparison. In these Examples, Ar represents the m-phenoxyphenyl radical so that, for example, $ArCH_3$ is m-phenoxytoluene, $ArCH_2Cl$ is m-phenoxybenzyl chloride and $ArCHCl_2$ is m-phenoxybenzal chloride.

EXAMPLE 1 m-Phenoxytoluene (173 g) and PCE (1163 ml) were stirred at 100° C., whilst Trigonox BPIC C75 (6 ml, 5.7 g) in PCE (557 ml) was added rapidly (BT 100°→77°). The mixture was heated to reflux (BT 123° C.) and stirred during the addition, over 2 hours, of sulphuryl chloride (160 ml) and Trigonox (12 ml) in PCE (1114 ml). After the addition, reflux was maintained for 1½ hours. The reaction mixture was cooled and quenched with caustic soda (10% aqueous, 1500 ml). The bottom organic layer was separated and washed with water (1500 ml). Evaporation of the PCE under reduced pressure gave the chlorinated reaction product (234 g).

COMPARATIVE EXAMPLE A m-Phenoxytoluene (184 g), PCE (1715 ml) and Trigonox (18 ml) were heated and stirred at reflux during the addition of sulphuryl chloride (160 ml) in PCE (1100 ml) over 2 hours. Reflux was maintained for 1½ hours after the addition and work-up as in Example 1 gave the chlorinated residue (208 g).

EXAMPLE 2 m-Phenoxytoluene (184 g, 1 mole) and PCE (1750 ml) were stirred at 100° C. whilst Trigonox (2.5 g) in PCE (250 ml) was added rapidly. The mixture was stirred at reflux during the addition, over 2 hours, of sulphuryl chloride (80 ml, 1 mole) and Trigonox (5 g) in PCE (500 ml). After the addition, reflux was maintained for ½ hour. Work-up as in Example 1 gave the chlorinated product (230 g).

EXAMPLE 3 m-Phenoxytoluene (184 g, 1 mole), PCE (2000 ml) and Trigonox BPIC C75 (2.5 g) were heated and stirred at reflux (121°–124° C.) for 5 mins, and then a solution of sulphuryl chloride (135 g, 1 mole), PCE (500 ml) and Trigonox BPIC C75 (5 g) was added dropwise over 2 hours, maintaining reflux and stirring. After the addition, reflux was continued for ½ hour and then the reaction mixture was cooled. A solution of aqueous sodium hydroxide (500 ml, 10% aqueous) was added and the mixture stirred for a further 1 hour. Separation gave a lower organic layer, which was evaporated under reduced pressure to give the chlorinated mixture as a residue.

EXAMPLE 4

Chlorine (89.5 g; 1.26 mole) was passed through m-phenoxytoluene (184 g; 1.0 mole) containing diphenyl sulphide (1 g; 0.0054 mole) over 4 hours at 230° C., with stirring. When the addition of chlorine was complete, nitrogen was passed through the reaction mixture for 30 minutes at 230° C.

EXAMPLE 5

Chlorine (47.5 g; 0.67 mole) was passed through m-phenoxytoluene (184 g; 1.0 mole) containing diphenyl sulphide (1 g; 0.0054 mole) over 5 hours at 250° C., with stirring. The reaction was carried out in a stainless steel vessel. When the addition of chlorine was complete, nitrogen was passed through the reaction mixture for 30 minutes at 250° C.

The following Table gives the analyses of products of each of the preceding Examples as obtained by nuclear magnetic resonance spectroscopy. Those compounds in the product other than the starting material and the desired chlorides were not differentiated in Examples 3 and 4, but the content of nuclear (Nuc) chlorinated compounds was determined for each of Examples 1, 2 and A. The amounts given in the Table are in weight percentages.

| Example | $ArCH_3$ | $ArCH_2Cl$ | $ArCHCl_2$ | Byproducts | Nuc. |
| --- | --- | --- | --- | --- | --- |
| 1 | 9.4 | 57.5 | 23.7 | 2.4 | 1.3 |
| A | 48.8 | 28.3 | 1.6 | 19.7 | 1.6 |
| 2 | 31.9 | 56.9 | 6.4 | 3.1 | 1.8 |
| 3 | 30.7 | 59.0 | 7.9 | 3.5 | |
| 4 | 54.5 | 35.0 | 5.0 | 5.5 | |

| Example | ArCH₃ | ArCH₂Cl | ArCHCl₂ | Byproducts | Nuc. |
|---------|-------|---------|---------|------------|------|
| 5 | 65.2 | 31.2 | 3.6 | | |

Comparison of the analyses of the products of Examples 1 and A will show that the gradual addition of initiator is preferable to its complete addition at the start of the reaction. Examples 2 and 3 show that good results can be achieved by using substantially equimolar amounts of m-phenoxytoluene and sulphuryl chloride and, although there is a high proportion of unconverted m-phenoxytoluene, this can be recycled as explained above. Examples 4 and 5 show the good results which can be obtained by the use of chlorine at a high temperature and a sulphur-containing catalyst.

EXAMPLE 6 m-Phenoxybenzyl chloride (218.5 g; 1 mole), sodium acetate (205 g; 2.5 mole), tetrabutylammonium bromide (10.9 g; 0.034 mole) and water (327 ml) were heated and stirred under reflux for 2 hours. On cooling m-Phenoxybenzyl acetate (241.5 g; 99.8% yield) separated as the upper layer. Its purity was 99%. m-Phenoxybenzyl acetate (242 g; 1 mole), sodium hydroxide (80 g; 2 mole), tetrabutylammonium bromide (12 g; 0.037 mole) and water (240 ml) were stirred at ambient temperature for 4 hours. The upper organic layer was dissolved in toluene (400 ml). The resulting solution was washed with water (2×200 ml) and treated with ion-exchange resin (Zerolit 236) and charcoal. Evaporation of the toluene gave the alcohol with a purity of 98.9% by gas chromatography (198 g, 99% yield).

The product of this Example may be converted to m-phenoxybenzaldehyde, as follows: m-phenoxybenzyl alcohol (25 g; 0.125 mole; 99% purity), ethyl acetate (370 ml), tetrabutylammonium hydrogen sulphate (0.0037 mole; 1.25 g) and sodium hypochlorite (370 ml, 10%, 0.5 mole) were stirred at 22°–23° C. for 2¼ hours. The upper organic layer was separated, washed with aqueous sodium carbonate (6×100 ml) and water (100 ml), dried (Na₂SO₄) and evaporated to give the aldehyde (21.4 g, 0.108 mole, 86% yield) of 97% purity (by G.L.C.).

We claim:

1. A process for preparing a mixture of m-phenoxybenzyl chloride and m-phenoxybenzal chloride, which comprises reacting m-phenoxytoluene with, per mole thereof, from one to 2 moles of sulphuryl chloride in an excess of perchloroethylene solvent and in the presence of an alkyl peralkanoate initiator, said initiator having a half-life of 1 to 60 minutes at 115° to 123° C., the sulphuryl chloride being added portionwise or continuously to the m-phenoxytoluene during the course of the reaction, in which the initiator is added to the reaction mixture in amounts of from 1 to 4% at the start of the reaction and from 2 to 10% during the course of the reaction, the percentages being by weight based on the weight of m-phenoxytoluene, said reaction being carried out under substantially atmospheric pressure and at a temperature of at least 110° C.

2. A process according to claim 1 in which the initiator is a tert-butyl peralkanoate of the formula R—CO—O—O—C(CH₃)₃, wherein R is $C_{1-12}$ alkyl or $C_{1-12}$ alkoxy.

3. A process according to claim 1 in which substantially equimolar proportions of m-phenoxytoluene and sulphuryl chloride are used.

4. A process according to claim 1 in which the initiator is added as a solution in the said solvent.

5. A process according to claim 1 in which the initiator is added together with the sulphuryl chloride during the course of the reaction.

6. A process according to claim 1 in which the initiator is selected from tert-butylperoxy isopropyl carbonate and tert-butyl peroctoate.

* * * * *